United States Patent
Maruyama

(10) Patent No.: US 11,042,746 B2
(45) Date of Patent: Jun. 22, 2021

(54) PRESENTING INFORMATION ON OBJECT TO BE OBSERVED

(71) Applicant: International Business Machines Corporation, Armonk, NY (US)

(72) Inventor: Daisuke Maruyama, Yamato (JP)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 16/432,083

(22) Filed: Jun. 5, 2019

(65) Prior Publication Data

US 2020/0387707 A1     Dec. 10, 2020

(51) Int. Cl.
    *G06K 9/00*             (2006.01)
    *A61B 5/0245*      (2006.01)
    *A61B 5/0205*      (2006.01)
    *A61B 5/00*            (2006.01)

(52) U.S. Cl.
    CPC ........ *G06K 9/00671* (2013.01); *A61B 5/0205* (2013.01); *A61B 5/0245* (2013.01); *A61B 5/743* (2013.01)

(58) Field of Classification Search
    CPC .......................... G06K 9/00671; A61B 5/0205; A61B 5/0245; A61B 5/743
    See application file for complete search history.

(56) References Cited

U.S. PATENT DOCUMENTS

| | | | |
|---|---|---|---|
| 2004/0230549 A1 | 11/2004 | Freer et al. | |
| 2014/0221776 A1 | 8/2014 | Stivoric et al. | |
| 2014/0351189 A1 | 11/2014 | Winn et al. | |
| 2015/0365600 A1* | 12/2015 | Pollack | H04N 5/2621 348/239 |
| 2017/0115726 A1 | 4/2017 | Fung | |
| 2018/0084338 A1* | 3/2018 | Bostick | H04R 3/005 |
| 2018/0174195 A1* | 6/2018 | Agarwal | G06Q 30/0261 |
| 2019/0213860 A1* | 7/2019 | Shaprio | H02J 7/025 |
| 2020/0258314 A1* | 8/2020 | Nonoyama | G06F 3/014 |

OTHER PUBLICATIONS

"What is iSeries?", Printed Jul. 27, 2018, 5 pages, <http://i-animal.jp>.
Aoki et al., "Park navigation system using smartphone", Intec Technical Journal, Printed Jun. 7, 2019, 13 pages.
Asahi et al., "Simulation of Crowd Optimization Using Personalized Schedules and Inducements", IPSJ SIG Technical Report, vol. 2015-ICS-178 No. 6, Mar. 2, 2015, 8 pages.

* cited by examiner

*Primary Examiner* — Grace Q Li
(74) *Attorney, Agent, or Firm* — Edward J. Wixted, III

(57) ABSTRACT

In an approach for presenting information on an object to be observed, a processor obtains information from a sensor about an object. A processor predicts a time period in which the object is expected to be at a location and in a state, based on historical data, obtained from the sensor, associated with the object. A processor determines whether the object is at the location and in the state within the time period. A processor presents information to a user, wherein the information is about the object.

20 Claims, 8 Drawing Sheets

PRESENTING INFORMATION ON OBJECT TO BE OBSERVED

BACKGROUND

The present invention relates generally to data collection and presentation of information, and more particularly to presenting superimposed information on an object to an observer.

Biological sensors are utilized for body measurements and calculations. Biological sensors may be used to collect data related to human or animal characteristics. Biological sensors may include, for example, heart rate monitors, electrical heart sensors, thermometers, and blood pressure sensors.

SUMMARY

Aspects of an embodiment of the present invention disclose a method, computer program product, and system for presenting information on an object to be observed, a processor obtains information from a sensor about an object. A processor predicts a time period in which the object is expected to be at a location and in a state, based on historical data, obtained from the sensor, associated with the object. A processor determines whether the object is at the location and in the state within the time period. A processor presents information to a user, wherein the information is about the object.

DETAILED DESCRIPTION

Figure 1:
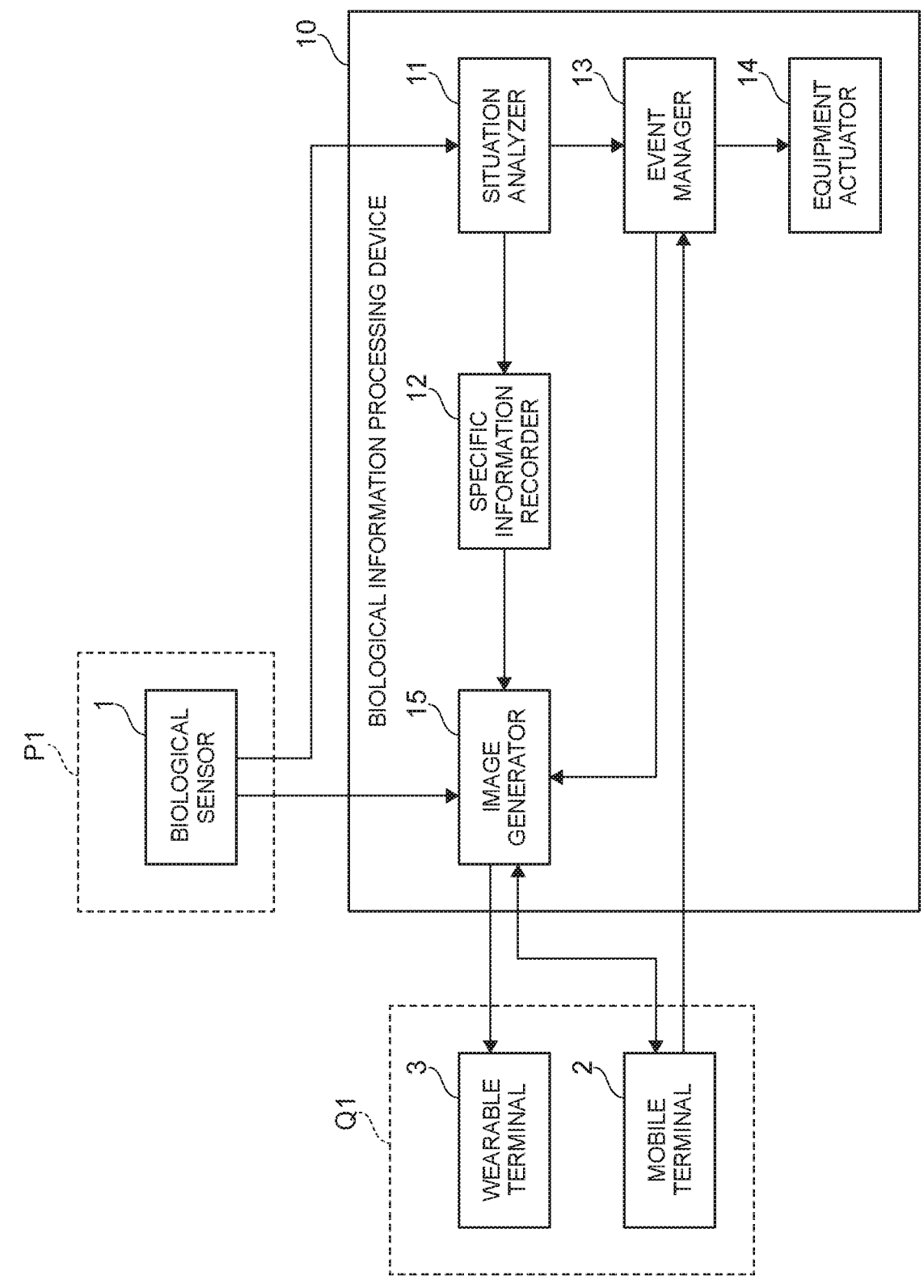
FIG. 1 depicts a block diagram of a system to which the some embodiments may be applied.

Hereinafter, exemplary embodiments of the present invention will be described in detail with reference to the attached drawings.

It is to be noted that embodiments of the present invention are not limited to the exemplary embodiments to be given below and may be implemented with various modifications within the scope of the present invention. In addition, the drawings used herein are for purposes of illustration, and may not show actual dimensions.

There are cases where an object is not in an anticipated situation at a given time despite that the object has been predicted to be in the anticipated situation at the given time. In such cases, an observer cannot observe the object in the predetermined situation at the given time.

Embodiments of the present invention predict a time period in which an object is in a specific situation, and in response to a detection that the object is not in the specific situation at the predicted time, during observation by an observer, presents information on the object from a past time period in which the object was in the specific situation (hereinafter, this information is referred to as "specific information") to the observer. Also, the some embodiments determine an event enabling the observer to observe the object in the predicted time period. Further, the exemplary embodiments take an action on the object in response to the event.

In some embodiments, the specific information includes an image of the object in the past time period in which the object was in the predetermined situation. In some embodiments, the specific information is superimposed on an image of the object at a current time.

A variety of embodiments will be described. While some include using a living thing (e.g., person, animal) as an example of the object, the object need not be alive.

In some embodiments, the object is a living thing.

Some embodiments may estimate or predict a situation, for example, a behavior, of a living thing, such as a human or animal, based on biological information sensed by a biological sensor, and present information to an observer of the living thing. Specifically, some embodiments may present real-time biological information on a living thing to an observer. In addition, some embodiments may record specific information on a specific situation of a living thing, and present the specific information to an observer when the observer cannot observe the living thing in the specific situation.

Also, some embodiments may generate event information indicating an event for an observer and a living thing. The event may be intended to enable the observer to observe the specific situation of the living thing at a good timing. That is, the event may be performed by the observer to enable him/herself to observe the object at a predicted time. Alternatively, the event may be performed by an entity to enable the observer to observe the object in a predicted time. The entity may be a person or an organization that causes the observer to observe the object.

Further, some embodiments may take an action on the living thing. The action may be intended to lead the living thing to the specific situation. The action may be taken to facilitate the observation of the object by the observer in a predicted time. Alternatively, the action may be taken to bring the object into a predetermined situation.

In reference to FIG. 1, the object is explained as a living thing P1 and the observer is explained as an observer Q1.

Referring to FIG. 1, there is shown a block diagram of a system in which some embodiments may be applied. As shown in FIG. 1, the system may include a biological sensor 1, a mobile terminal 2, a wearable terminal 3, and a biological information processing device 10. Since the biological sensor 1 can be worn by, or otherwise affixed to, the living thing P1, the biological sensor 1 is shown within a broken line representing the living thing P1. Since the mobile terminal 2 and the wearable terminal 3 can be carried and/or worn by the observer Q1, each of the mobile terminal 2 and the wearable terminal 3 is shown within a broken line representing the observer Q1.

The biological sensor 1 may sense biological information about the living thing P. The biological sensor 1 may be attached to the living thing P1 in a contact state or in a non-contact state. The biological sensor 1 may be, for example, a temperature sensor, a blood pressure sensor, an electrocardiogram sensor, or the like.

The mobile terminal 2 may be a terminal device carried by the observer Q1. For example, the mobile terminal 2 may be a smart phone. The mobile terminal 2 is assumed to have a function of superimposing, on the real image displayed on its screen using its camera, an image generated by the biological information processing device 10 utilizing, for example, augmented reality (AR) techniques.

The wearable terminal 3 may be a terminal device worn by the observer Q1. For example, the wearable terminal 3 may be a smart glass or an optical see-through head mount display (HMID). The wearable terminal 3 is assumed to have a function of superimposing, on the real image that can be seen through eyeglasses, an image generated by the biological information processing device 10, utilizing, for example, AR techniques.

Note that, although the mobile terminal 2 and the wearable terminal 3 are provided in some embodiments, it is not always necessary to provide both the mobile terminal 2 and the wearable terminal 3.

The biological information processing device 10 may process the biological information sensed by the biological sensor 1 and perform various operations based on the processing result. The biological information processing device 10 may include a situation analyzer 11, a specific information recorder 12, an event manager 13, an equipment actuator 14, and an image generator 15.

The situation analyzer 11 may obtain the biological information from the biological sensor 1. The situation analyzer 11 may use the biological information to detect or predict a situation of the living thing P1 based on the biological information.

The specific information recorder 12 may record specific information on the living thing P1 when the situation analyzer 11 detects a specific situation from the biological information. Alternatively, the specific information recorder 12 may record specific information on the living thing P1 when the current time reaches a time (including a time period) which has been predicted to be a time when the living thing P1 is in a specific situation. The specific information on the living thing P1 may be biological information sensed by the biological sensor 1, a video or imagine taken by a camera connected to the biological information processing device 10, and the like.

The event manager 13 may generate event information indicating a new event or modify event information indicating an existing event based on prediction of the situation of the living thing P1 by the situation analyzer 11, a schedule of the observer Q1, or the like. The generation or modification of the event information may be performed at a predetermined time based on historical data used to generate a prediction of the situation of the living thing P1. For example, the event information indicating an event for a particular day may be generated or modified on the morning of that particular day. Alternatively, the generation or modification of the event information may be performed based on the prediction of the situation of the living thing P1 each time the prediction is made.

The equipment actuator 14 may actuate equipment related to the living thing P1 to take some kind of action on the living thing P1 depending on the event information. "Some kind of action" is ideally an approach to lead the living thing P1 to the specific situation, but it is not limited to the approach. Further, the equipment actuator 14 may take succeeding actions on the living thing P1, using an assessment by the situation analyzer 11 of the influence of the result of the action on the specific situation.

The image generator 15 may generate an image to be superimposed on a real image, when the observer Q1 is at an observation place, namely a place where the observer Q1 can typically observe the living thing P1. The determination that the observer Q1 is in the observation place can be made using a GPS function of the mobile terminal 2 in possession of the observer Q1. The superimposed image may include real-time biological information obtained from the biological sensor 1. If the living thing P1 is not in the specific situation, the superimposed image may further include the specific information at a time when the living thing P1 was at the specific situation, which may be recorded by the specific information recorder 12. The image generator 15 may transmit the superimposed image to the mobile terminal 2 or the wearable terminal 3 of the observer Q1. Alternatively, the image generator 15 may generate a superimposed image including the event information generated by the event manager 13, and transmit the superimposed image to the mobile terminal 2 or the wearable terminal 3 of the observer Q1. The superimposed image may be an AR image or a mixed reality (MR) image. Further, when the specific information recorder 12 has recorded a video, as the specific information on the living thing P1, the AR image or the MR image may be an AR video or an MR video.

Next, an operation of the biological information processing device 10 according to some embodiments is described.

Figure 2:
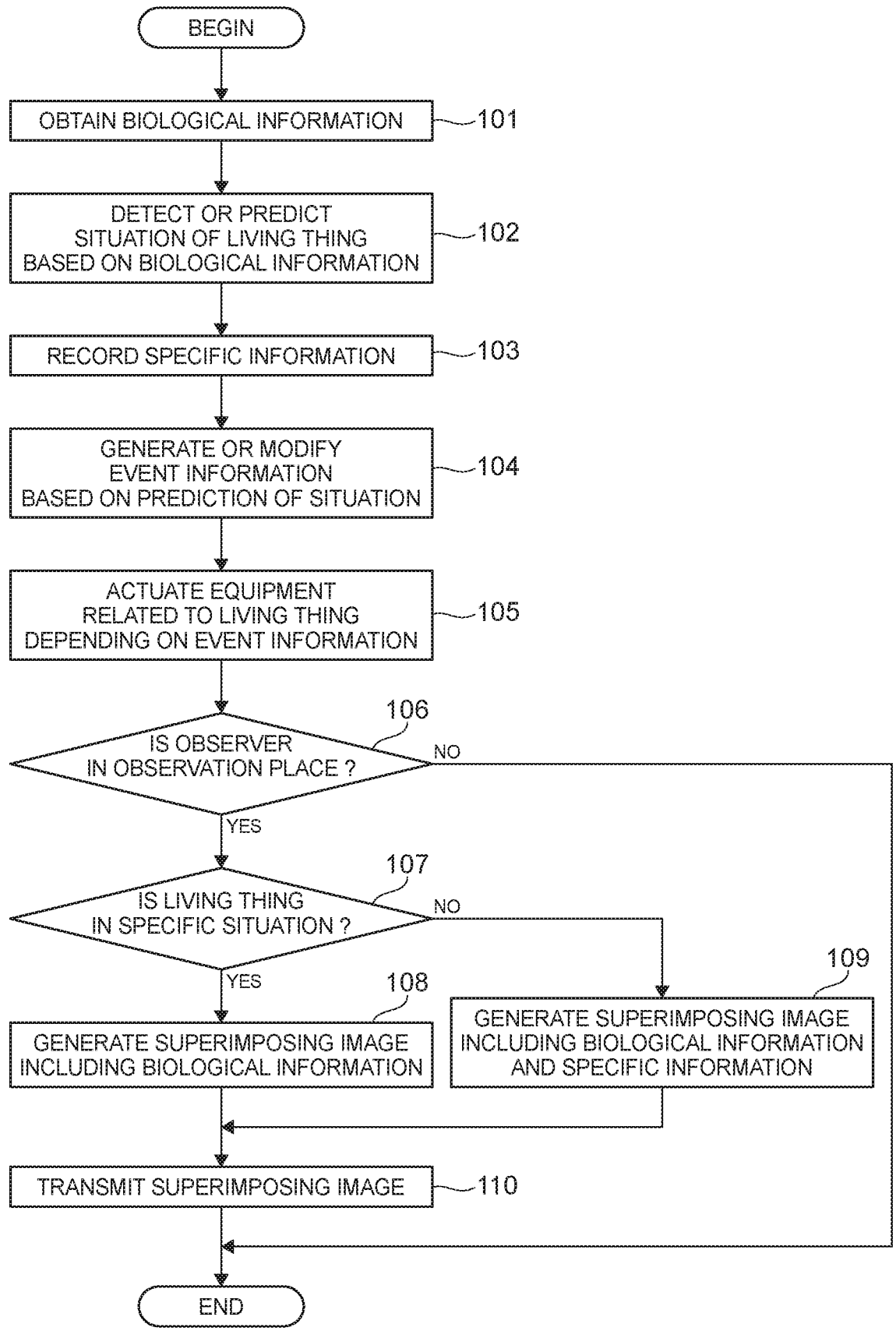
FIG. 2 depicts a flowchart representing an example of an operation performed by a biological information processing device in some embodiments.

Referring to FIG. 2, there is shown a flowchart representing an example of an operation performed by the biological information processing device 10.

First, the situation analyzer 11 and the image generator 15 may obtain the biological information from the biological sensor 1 (step 101). After this, the situation analyzer 11 and the image generator 15 may obtain the biological information successively from the biological sensor 1.

Then, the situation analyzer 11 may detect or predict the situation of the living thing P1 based on the biological information obtained at step 101 (step 102).

Next, the specific information recorder 12 may record the specific information on the living thing P1, at a time when the situation analyzer 11 detects a specific situation at step 102, or at a time which has been predicted to be a time when the living thing P1 is in the specific situation at step 102 (step 103).

Next, the event manager 13 may generate or modify the event information based on the prediction of the situation of the living thing P1 at step 102, a schedule of the observer Q1 or the like (step 104).

Subsequently, the equipment actuator 14 may actuate equipment related to the living thing P1 depending on the event information generated or modified at step 104 (step 105).

After that, the image generator 15 may determine whether or not the observer Q1 is in an observation place (step 106).

If the observer Q1 is determined to be in the observation place at step 106, the image generator 15 may determine whether or not the living thing P1 is in the specific situation based on any of the biological information obtained successively after step 101 (step 107).

If the living thing P1 is determined to be in the specific situation at step 107, the image generator 15 may generate a superimposing image including any of the biological information obtained successively after step 101 (step 108). On the other hand, if living thing P1 is not determined to be in the specific situation at step 107, the image generator 15 may generate a superimposing image including any of the biological information obtained successively after step 101 and the specific information on the living thing P1 recorded by the specific information recorder 12 at step 103 (step 109).

Then, the image generator 15 may transmit the superimposing image to the mobile terminal 2 or the wearable terminal 3 (step 110), and end the process of FIG. 2.

Note that if the observer Q1 is not determined to be in the observation place at step 106, the image generator 15 may end the process of FIG. 2 without generating any superimposing image.

Other embodiments may be applied to medical treatment.

If a patient is sleeping or does not have symptoms in either a hospital or home-visit medical treatment environment, a doctor who visits the patient may not be able to examine the patient appropriately. For example, the doctor may not want to wake up the sleeping patient. Thus, the visit of the visiting doctor may be wasteful and inefficient.

Embodiments may show the visiting doctor the patient's real-time biological information, using a biological sensor operably affixed to the patient. Specifically, some embodiments may analyze the biological information and record the specific information at a time when the patient has been in the specific situation. Then, embodiments may show the visiting doctor a specific situation different from the present situation, by presenting specific information with the biological information from the biological sensor when the patient does not have symptoms during the visit of the visiting doctor.

Also, some embodiments may analyze the biological information from the biological sensor, predict the timing of sleep or appearance of symptoms, and plan an appropriate schedule of a visit event based on the prediction, the visiting doctor's schedule and other patients' situations.

Further, an embodiment may take an action, such as raising of a bed of the patient, depending on the visit event, as long as the patient's physical condition permits.

Patients may be permitted to opt-in or opt-out of any of the services described herein. Biological devices and other biological information should not be used without the express consent of the patient, nor should information be obtained from the patient that goes beyond the scope of consent.

In an embodiment, the object is explained as a patient P2, and the observer is explained as a visiting doctor Q2. In addition, the predetermined situation is explained as a predetermined physical state of the patient P2.

Figure 3:
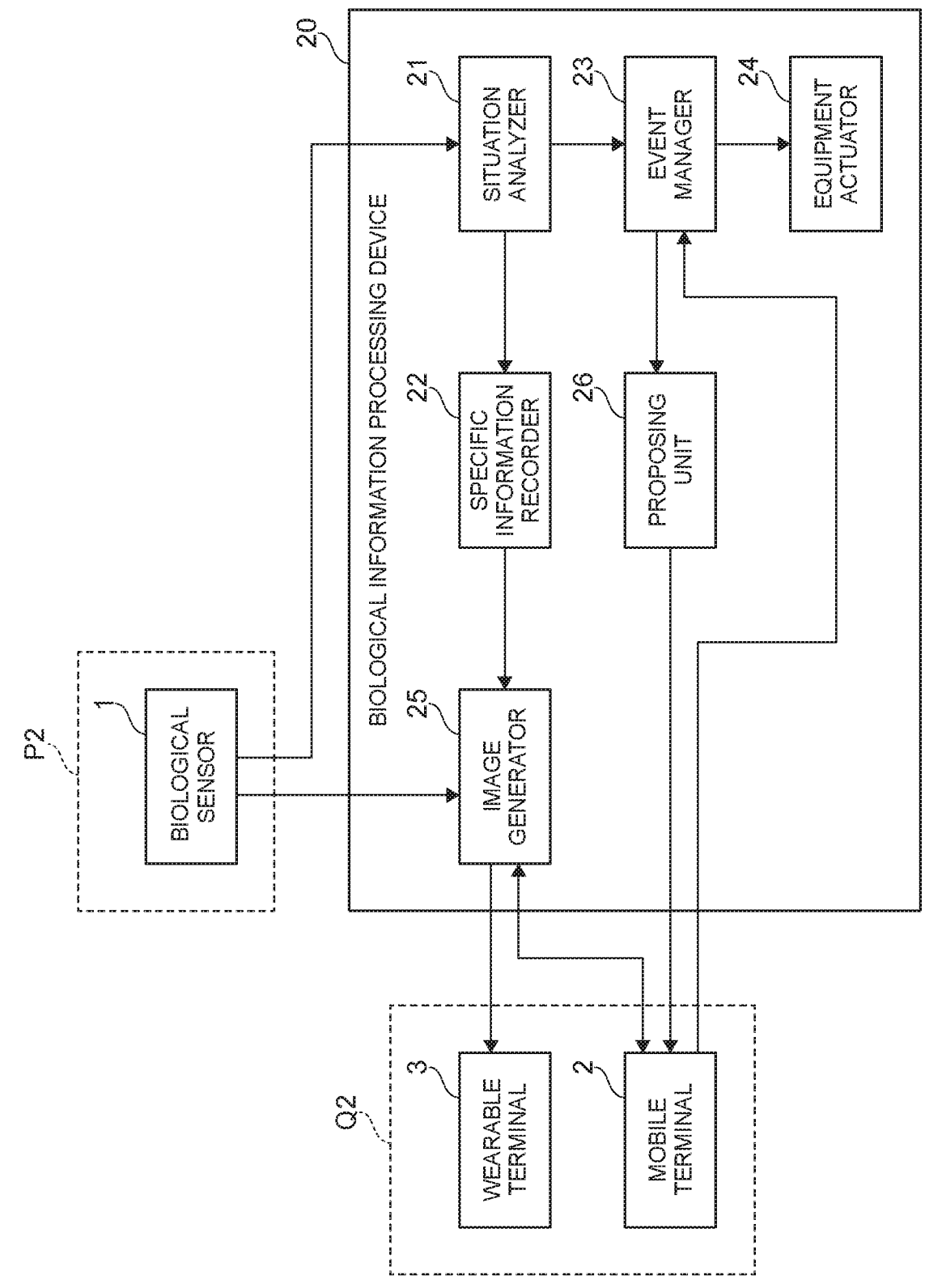
FIG. 3 depicts a block diagram of a system to which some embodiments may be applied.

Referring to FIG. 3, there is shown a block diagram of a system to which an embodiment is applied. As shown in FIG. 3, the system may include a biological sensor 1, a mobile terminal 2, a wearable terminal 3, and a biological information processing device 20. Since the biological sensor 1 can be operably affixed to the patient P2, it is shown in a broken line, indicating the patient P2. Since the mobile terminal 2 and the wearable terminal 3 can be carried or worn by the visiting doctor Q2, they are shown in a broken line, indicating the visiting doctor Q2.

The biological sensor 1 may sense biological information on the patient P2. The biological sensor 1 may be attached to the patient P2 in a contact state or in a non-contact state. The biological sensor 1 may be, for example, a temperature sensor, a blood pressure sensor, an electrocardiogram sensor and the like.

The mobile terminal 2 may be a terminal device carried by the visiting doctor Q2. For example, a smart phone may be used as the mobile terminal 2. The mobile terminal 2 is assumed to have a function of superimposing, on the real image displayed on its screen using its camera, an image generated by the biological information processing device 20.

The wearable terminal 3 may be a terminal device worn by the visiting doctor Q2. For example, a smart glass or an optical see-through head mount display (HMID) may be used as the wearable terminal 3. The wearable terminal 3 is assumed to have a function of superimposing, on the real image that can be seen through eyeglasses, an image generated by the biological information processing device 20.

Note that, although the mobile terminal 2 and the wearable terminal 3 are provided in some embodiments, it is not always necessary to provide both the mobile terminal 2 and the wearable terminal 3.

The biological information processing device 20 may process the biological information sensed by the biological sensor 1 and perform various operations based on the processing result. The biological information processing device 20 may include a situation analyzer 21, a specific information recorder 22, an event manager 23, an equipment actuator 24, an image generator 25, and a proposing unit 26.

The situation analyzer 21 may obtain the biological information from the biological sensor 1. Then, the situation analyzer 21 may detect or predict a predetermined specific situation of the patient P2 based on the biological information. The predetermined specific situation may be, for example, a situation in which the patient P2 is having a seizure or a symptom, a situation in which the patient P2 is awake or asleep, or the like.

The specific information recorder 22 may record specific information on the patient P2 when the situation analyzer 21 detects the specific situation from the biological information. Alternatively, the specific information recorder 22 may record specific information on the patient P2 when the current time reaches a time (including a time period) which has been predicted to be a time when the patient P2 is in the specific situation. The specific information on the patient P2 may be biological information sensed by the biological sensor 1, a video taken by a camera connected to the biological information processing device 20, and the like.

The event manager 23 may generate or modify visit event information indicating the times of visit events based on prediction of the situation of the patient P2 by the situation analyzer 21, the current location or a schedule of the visiting doctor Q2 or the like. Information input by the visiting doctor Q2 to the mobile terminal 2 may be used as the current location or the schedule of the visiting doctor Q2. The generation or modification of the visit event information may be performed at a predetermined timing based on the prediction of the situation of the patient P2 accumulated up to then. For example, the visit event information indicating a visit event for a day may be generated or modified on the morning of the day. Alternatively, the generation or modification of the visit event information may be performed based on the prediction of the situation of the patient P2 each time the prediction is performed. For example, the event manager 23 may generate the visit event information as follows: (1) generate the visit event information indicating the visit event where the visiting doctor Q2 visits the patient P2 at a visiting time predicted to be a time when the patient P2 is in the specific situation; (2) if the visiting doctor Q2 cannot visit the patient P2 at the visiting time for the reason that the patient P2's home is distant from the current location of the visiting doctor Q2 or for the reason that the visiting doctor Q2 has another plan at the visiting time, modify the visit event information for the patient P2; (3) if plural visit events for plural patients P2 overlap with each other, modify the visit event information such that the visiting doctor Q2 visits the plural patients P2 sequentially from the one closest to the current location of the visiting doctor Q2.

The equipment actuator 24 may actuate equipment related to the patient P2 to take some kind of action on the patient P2 depending on the visit event information. The equipment related to the patient P2 may be a notification device for notifying that meal should be prepared, a bed of the patient P2, or the like. For example, the equipment actuator 24 may take an action, such as suggesting of preparing meal using the notification device, or raising of the bed, if the current time is a predetermined time before the visiting time for the patient P2 defined by the visit event information generated by the event manager 23.

The image generator 25 may generate a superimposing image to be superimposed on a real image, when the visiting doctor Q2 is in the patient P2's home, namely a place where the visiting doctor Q2 can examine the patient P2. The determination that the visiting doctor Q2 is in the patient P2's home can be made using a GPS function of the mobile terminal 2 held by the visiting doctor Q2. The superimposing image may include real-time biological information obtained from the biological sensor 1. By using the biological information obtained from the biological sensor 1, it is also possible to determine whether the patient P2 is in a serious state (e.g., at serious health risk) or simply in a sleeping state. If the patient P2 is not in the specific situation, the superimposing image may further include the specific information at a time when the patient P2 has been in the specific situation, which is recorded by the specific information recorder 22. Then, the image generator 25 may transmit the superimposing image to the mobile terminal 2 or the wearable terminal 3 of the visiting doctor Q2. The superimposing image may be an image generally called an augmented reality (AR) image or a mixed reality (MR) image. Further, when the specific information recorder 22 has recorded a video as the specific information on the patient P2, the AR image or the MR image may be an AR video image or an MR video.

The proposing unit 26 may generate proposal information for proposing a visiting order of plural patients P2' homes, a traveling route via the plural patients P2' homes, and the like depending on the visit event information generated or modified by the event manager 23, and present the proposal information. For example, the proposing unit 26 may determine the visiting order by arranging the plural patients P2' homes defined in the visit event information to be visited at almost the same time from the one closest to the current location of the visiting doctor Q2. At that time, the proposing unit 26 may determine the traveling route with reference to map information (not shown).

Figure 4:
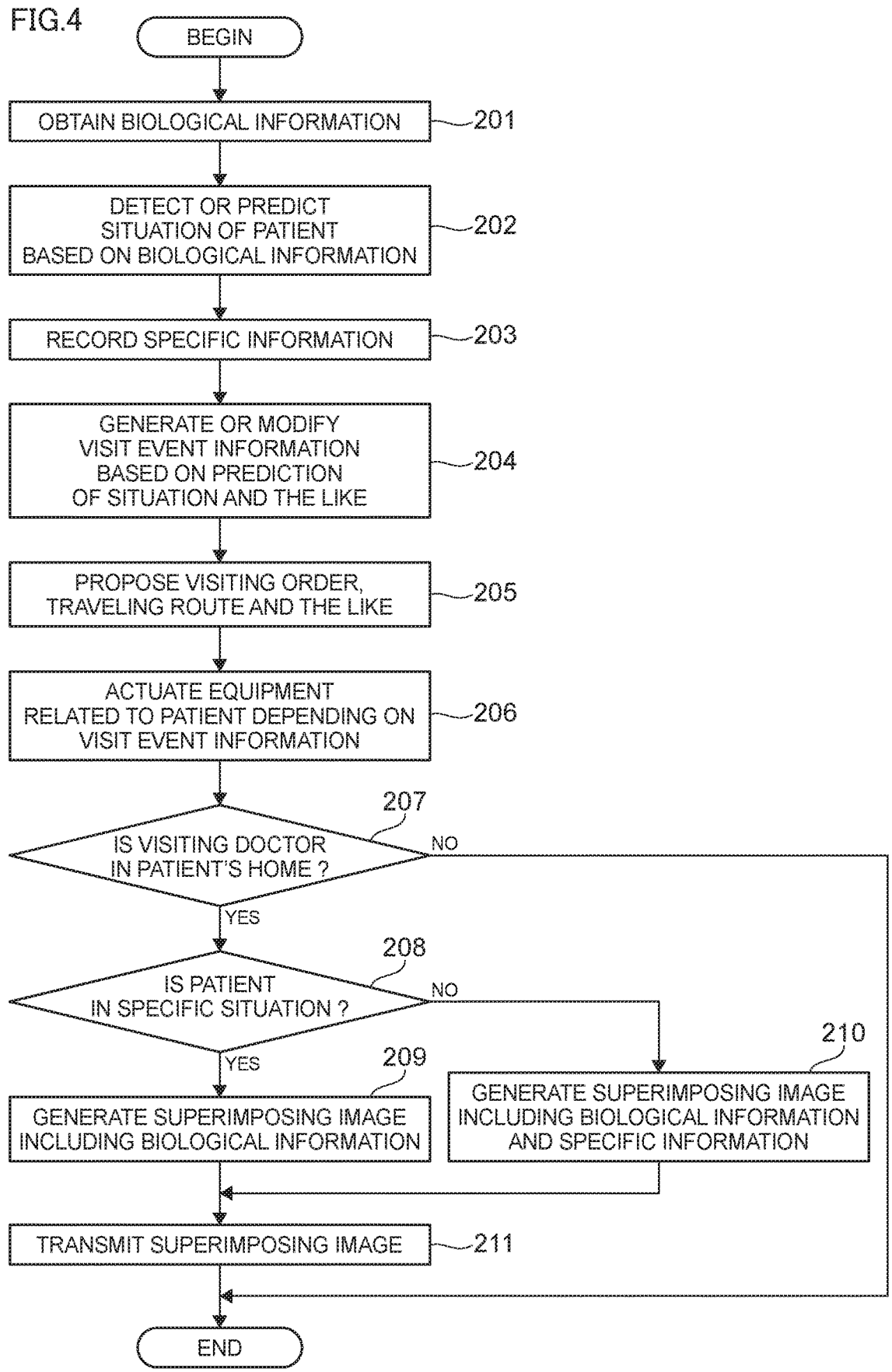
FIG. 4 depicts a flowchart representing an example of an operation performed by a biological information processing device in some embodiments.

Referring to FIG. 4, there is shown a flowchart representing an example of an operation performed by the biological information processing device 20. While the example describes a doctor patient home visit, it should be noted that a similar process could be performed regarding an in-patient hospital stay.

The situation analyzer 21 and the image generator 25 may obtain the biological information from the biological sensor 1 (step 201). After this, the situation analyzer 21 and the image generator 25 may obtain the biological information successively from the biological sensor 1.

Then, the situation analyzer 21 may detect or predict the situation of the patient P2 based on the biological information obtained at step 201 (step 202).

Next, the specific information recorder 22 may record the specific information on the patient P2, at a time when the situation analyzer 21 detects a specific situation at step 202, or at a time which has been predicted to be a time when the patient P2 is in the specific situation at step 202 (step 203).

Next, the event manager 23 may generate or modify the visit event information based on the prediction of the situation of the patient P2 at step 202, a schedule of the visiting doctor Q2 and the like (step 204).

Next, the proposing unit 26 may generate and propose a visiting order of plural patients P2' homes, a traveling route via the plural patients P2' homes and the like (step 205).

Subsequently, the equipment actuator 24 may actuate equipment related to the patient P2 depending on the visit event information generated or modified at step 204 (step 206).

After that, the image generator 25 may determine whether or not the visiting doctor Q2 is in the patient P2's home (step 207).

If the visiting doctor Q2 is determined to be in the patient P2's home at step 207, the image generator 25 may determine whether or not the patient P2 is in the specific situation based on any of the biological information obtained successively after step 201 (step 208).

If the patient P2 is determined to be in the specific situation at step 208, the image generator 25 may generate a superimposing image including any of the biological information obtained successively after step 201 (step 209). On the other hand, if the patient P2 is not determined to be in the specific situation at step 208, the image generator 25 may generate a superimposing image including any of the biological information obtained successively after step 201 and the specific information on the patient P2 recorded by the specific information recorder 22 at step 203 (step 210).

Then, the image generator 25 may transmit the superimposing image to the mobile terminal 2 or the wearable terminal 3 (step 211), and end the process of FIG. 4.

Note that if the visiting doctor Q2 is not determined to be in the patient P2's home at step 207, the image generator 25 may end the process of FIG. 4 without generating any superimposing image.

Some embodiments may be applied to animals and visitors in a zoo or animal shelter (terms used interchangeably herein).

Recent zoos commonly provide not only morphological exhibition of a single kind of animal in a narrow area surrounded by fences and cages, but also behavioral exhibition of multiple kinds of animals in a wide area imitating a grassland or a forest. However, there are circumstances that are not preferable when visitors observe animals, such as where a visitor is unable to find certain animals, animals cannot be observed because they are being hidden by obstacles, or animals are sleeping.

An embodiment may present to a visitor real-time biological information on an animal visible from a place of the visitor, using a biological sensor and a GPS receiver operably affixed to the animal. In addition, an embodiment may record specific information at a time when the animal is in a specific situation. An embodiment may present the specific information when the animal is not in the specific situation while the visitor observes the animal. For example, an embodiment may analyze using a biological sensor a situation such as where an animal is sleeping at a place invisible from the visitor, and present a past video in which the animal is active at a location where the animal is frequently active.

Also, an embodiment may determine effectively a place and time of an exhibition event by analyzing the biological information on the animal and predicting a situation of the animal, and present a recommended route to the visitor.

Specifically, an embodiment may determine and present the recommended route based on information on a plurality of visitors (e.g., their favorite animals and schedules), existing events, and a congestion situations.

Further, an embodiment may take an action on the animal depending on the exhibition event. For example, an embodiment may feed the animal and announce the feeding of the animal in an area predicted not to be crowded during a time period when the animal is awake but not expected to be active, and thus equalize congestion in the zoo.

In an embodiment, the object is explained as an animal P3, and the observer is explained as a visitor Q3. In addition, the predetermined situation is explained as a predetermined physical state of the animal P3, and the entity enabling the observer to observe the object is explained as a handler of the animal P3.

Figure 5:
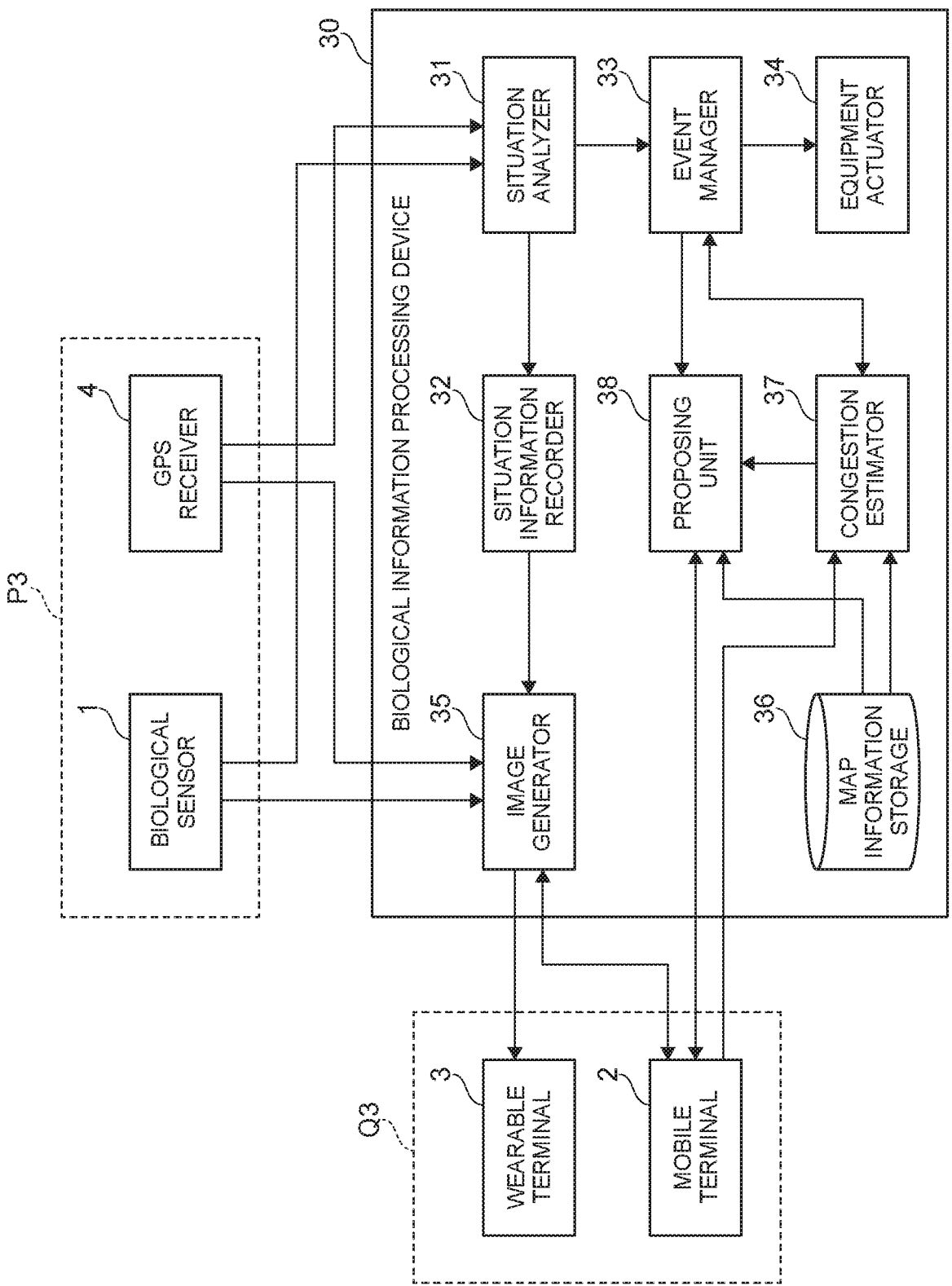
FIG. 5 depicts a block diagram of a system to which some embodiments may be applied.

Referring to FIG. 5, there is shown a block diagram of a system to which an embodiment is applied. As shown in FIG. 5, the system may include a biological sensor 1, a mobile terminal 2, a wearable terminal 3, a GPS receiver 4, and a biological information processing device 30. Since the biological sensor 1 and the GPS receiver 4 can be operably affixed to the animal P3, it is shown in a broken line indicating the animal P3, and since the mobile terminal 2 and the wearable terminal 3 can be carried or worn by the visitor Q3, they are shown in a broken line indicating the visitor Q3.

The biological sensor 1 may sense biological information on the animal P3. The biological sensor 1 may be attached to the animal P3 in a contact state or in a non-contact state. The biological sensor 1 may be, for example, a temperature sensor, a blood pressure sensor, an electrocardiogram sensor and the like.

The mobile terminal 2 may be a terminal device carried by the visitor Q3. For example, a smart phone may be used as the mobile terminal 2. The mobile terminal 2 is assumed to have a function of superimposing, on the real image displayed on its screen using its camera, an image generated by the biological information processing device 30.

The wearable terminal 3 may be a terminal device worn by the visitor Q3. For example, a smart glass or an optical see-through head mount display (HMID) may be used as the wearable terminal 3. The wearable terminal 3 is assumed to have a function of superimposing, on the real image that can be seen through eyeglasses, an image generated by the biological information processing device 30.

Note that, although the mobile terminal 2 and the wearable terminal 3 are provided in some embodiments, it is not always necessary to provide both the mobile terminal 2 and the wearable terminal 3.

The GPS receiver 4 may sense location information indicating a location of the animal P3. The GPS receiver 4 may be attached to the animal P3.

The biological information processing device 30 may process the biological information sensed by the biological sensor 1 and perform various operations based on the processing result. The biological information processing device 30 may include a situation analyzer 31, a specific information recorder 32, an event manager 33, an equipment actuator 34, an image generator 35, a map information storage 36, a congestion estimator 37, and a proposing unit 38.

The situation analyzer 31 may obtain the biological information from the biological sensor 1, and obtain the location information from the GPS receiver 4. Then, the situation analyzer 31 may detect or predict a predetermined specific situation of the animal P3 based on the biological information and the location information. The predetermined specific situation may be, for example, a situation in which the animal P3 is awake, a situation in which the animal P3 is moving, a situation in which the animal P3 is active, or the like.

The specific information recorder 32 may record specific information on the animal P3 when the situation analyzer 31 detects the specific situation from the biological information and the location information. Alternatively, the specific information recorder 32 may record specific information on the animal P3 when the current time reaches a time (including a time period) which has been predicted to be a time when the animal P3 is in the specific situation. The specific information on the animal P3 may be biological information sensed by the biological sensor 1, location information sensed by the GPS receiver 4, a video taken by a camera connected to the biological information processing device 30, and the like.

The event manager 33 may generate or modify exhibition event information indicating executions and times of exhibition events based on prediction of the situation of the animal P3 by the situation analyzer 31, prediction of congestion of the zoo by the congestion estimator 37, or the like. The exhibition event information may indicate, for example, feeding of the animal P3, movement of an exhibition place inside an exhibition area of the animal P3, presentation by a handler of the animal P3, or the like. The generation or modification of the exhibition event information may be performed at a predetermined timing based on the prediction of the situation of the animal P3 accumulated up to then. For example, the exhibition event information indicating an exhibition event for a day may be generated or modified on the morning of the day. Alternatively, the generation or modification of the exhibition event information may be performed based on the prediction of the situation of the animal P3 each time the prediction is performed. For example, the event manager 33 may generate the exhibition event information of the animal P3 by determining when the animal P3 is awake and a degree of congestion in front of the animal P3's exhibition place is low.

The equipment actuator 34 may actuate equipment related to the animal P3 to take some kind of action on the animal P3 depending on the exhibition event information. The equipment related to the animal P3 may be a feeding machine, a lighting device, or the like. For example, the equipment actuator 34 may take an action, such as feeding using the feeding machine or adjustment of the lighting device, if the current time is a predetermined time before the exhibition time of the animal P3 defined by the exhibition event information generated by the event manager 33.

The image generator 35 may generate a superimposing image to be superimposed on a real image, when the visitor Q3 is in front of the animal P3's exhibition place, namely a place where the visitor Q3 intends to observe the animal P3. The determination that the visitor Q3 is in front of the animal P3's exhibition place can be made using a GPS function of the mobile terminal 2 held by the visitor Q3. The superimposing image may include real-time biological information obtained from the biological sensor 1. The superimposing image may also include presence information indicating the presence of the animal P3 at a part of the real image, calculated based on locations of the animal P3 and the visitor Q3 obtained using a GPS function, and map information stored in the map information storage 36. Thereby, the visitor Q3 can recognize the presence of the animal P3, even if the visitor Q3 cannot observe the animal P3 for the reason that there is a tree or the like between the animal P3 and the visitor Q3. If the animal P3 is not in the specific situation, the superimposing image may further include the specific information at a time when the animal P3 has been in the specific situation, which is recorded by the specific information recorder 32. Then, the image generator 35 may transmit the superimposing image to the mobile terminal 2 or the wearable terminal 3 of the visitor Q3. The superimposing image may be an image generally called an augmented reality (AR) image or a mixed reality (MR) image. Further, when the specific information recorder 32 has recorded a video as the specific information on the animal P3, the AR image or the MR image may be an AR video or an MR video.

The map information storage 36 may store map information indicating a map of the zoo.

The congestion estimator 37 may estimate a degree of congestion in the zoo in the future based on locations and schedules of visitors Q3 and schedules of existing events. For example, the congestion estimator 37 may estimate the degree of congestion as follows: (1) obtain the locations and schedules of the visitors Q3 from the mobile terminals 2 of the visitors Q3; (2) specify current locations of the visitors Q3 based on the locations obtained from the mobile terminals 2 of the visitors Q3 and the map information stored in the map information storage 36, and specify future locations of the visitors Q3 based on the schedules obtained from the mobile terminals 2 of the visitors Q3 and the map information stored in the map information storage 36; (3) count the number of visitors Q3 who are in front of each animal P3's exhibition place of the animal P3 for each unit time; (4) obtain schedules of the existing events of each animal P3's exhibition place for each unit time; (5) calculate the degree of congestion based on the number of visitors Q3 and the schedules of the existing events, for each animal P3's exhibition place and for each unit time.

The proposing unit 38 may obtain from the mobile terminal 2 of the visitor Q3 information such as a location and a schedule of the visitor Q3, a traveling history of the visitor Q3 at past visits, an age of the visitor Q3, a favorite animal of the visitor Q3, whether or not the visitor Q3 has an annual pass, or the like. Then, the proposing unit 38 may generate and propose a recommended route of each visitor Q3 (e.g., what time and to which exhibition event each visitor Q3 is recommended to go) based on the degree of congestion estimated by the congestion estimator 37 and the information on the visitors Q3. For example, the proposing unit 38 may generate the recommended route as follows: (1) specify an animal P3's exhibition place which the visitor Q3 stops by for each unit time based on the location and the schedule of the visitor Q3; (2) compare the animal P3's exhibition place which the visitor Q3 stops by with another animal P3's exhibition place where the exhibition event is executed for each unit time, and determine a latter animal P3's exhibition place as a candidate exhibition place if the former animal P3's exhibition place is close to the latter animal P3's exhibition place; (4) determine the candidate exhibition place as a recommended animal P3's exhibition place, by referring to information such as the location and the schedule of the visitor Q3, the traveling history of the visitor Q3 at the past visits, the age of the visitor Q3, the favorite animal of the visitor Q3, whether or not the visitor Q3 has the annual pass, or the like; (5) does not determine the candidate exhibition place as a recommended animal P3's exhibition place, if the degree of congestion is not equal by changing the traveling route to stop by the candidate exhibition.

Next, an operation of the biological information processing device 30 according to an embodiment is described.

Figure 6:
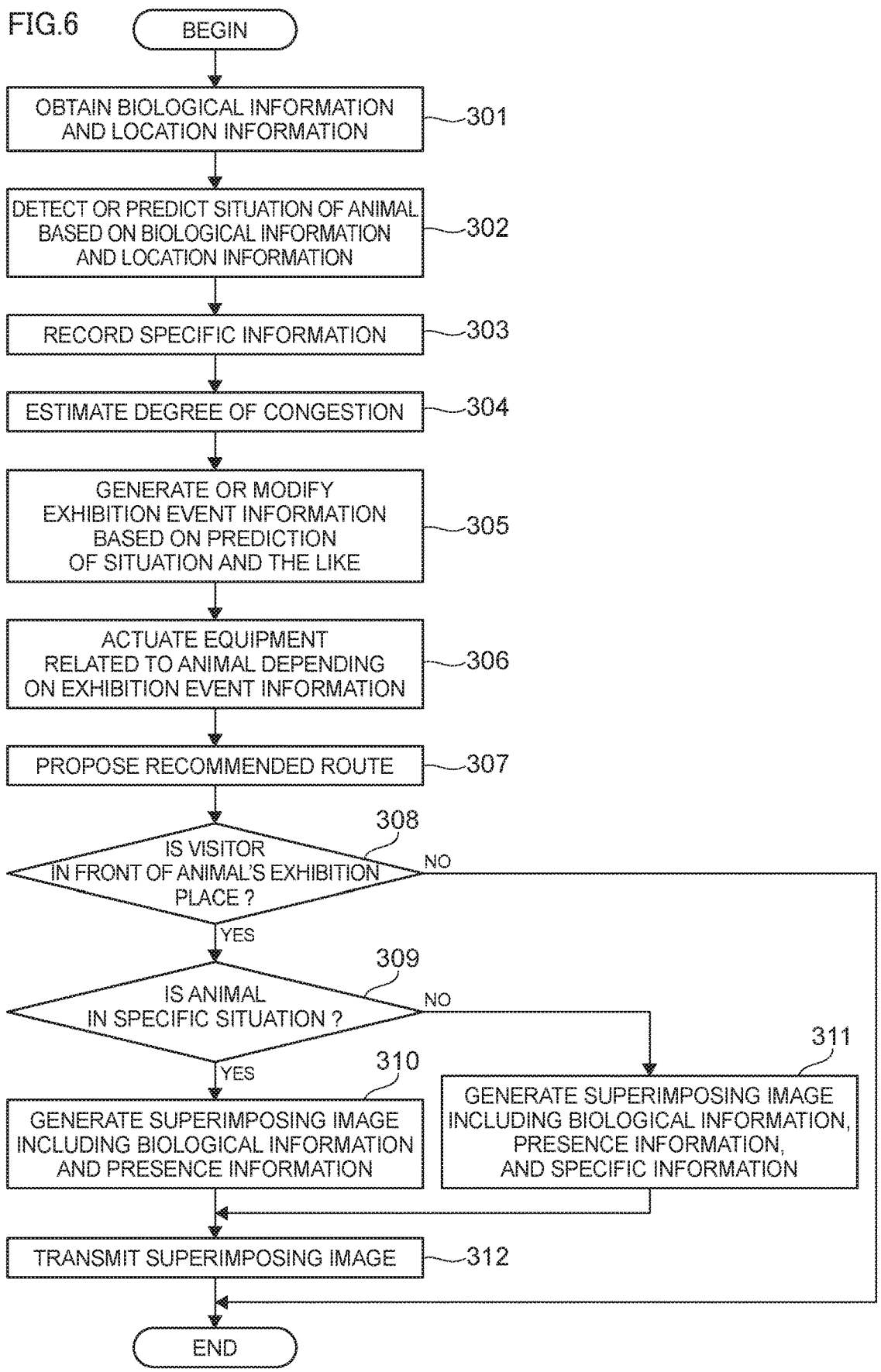
FIG. 6 depicts a flowchart representing an example of an operation performed by a biological information processing device in some embodiments.

Referring to FIG. 6, there is shown a flowchart representing an example of an operation performed by the biological information processing device 30.

First, the situation analyzer 31 and the image generator 35 may obtain the biological information from the biological sensor 1, and obtain the location information from the GPS receiver 4 (step 301). After this, the situation analyzer 31 and the image generator 35 may obtain the biological information successively from the biological sensor 1, and obtain the location information successively from the GPS receiver 4.

Then, the situation analyzer 31 may detect or predict the situation of the animal P3 based on the biological information and the location information obtained at step 301 (step 302).

Next, the specific information recorder 32 may record the specific information on the animal P3, at a time when the situation analyzer 31 detects a specific situation at step 302, or at a time which has been predicted to be a time when the animal P3 is in the specific situation at step 302 (step 303).

Next, the congestion estimator 37 may estimate the degree of congestion in the zoo in the future based on the locations and the schedules of the visitors Q3, the schedules of the existing events, or the like (step 304).

Next, the event manager 33 may generate or modify the exhibition event information based on the prediction of the situation of the animal P3 at step 302, the prediction of the degree of congestion in the zoo in the future at step 304, and the like (step 305).

Subsequently, the equipment actuator 34 may actuate equipment related to the animal P3 depending on the exhibition event information generated or modified at step 305 (step 306).

Next, the proposing unit 38 may generate and propose the recommended route for each visitor Q3 based on the prediction of the degree of congestion in the zoo in the future at step 304, information on the visitors Q3, or the like (step 307).

After that, the image generator 35 may determine whether or not the visitor Q3 is in front of the animal P3's exhibition place (step 308).

If the visitor Q3 is determined to be in front of the animal P3's exhibition place at step 308, the image generator 35 may determine whether or not the animal P3 is in the specific situation based on any of the biological information and any of the location information obtained successively after step 301 (step 309).

If the animal P3 is determined to be in the specific situation at step 309, the image generator 35 may generate a superimposing image including any of the biological information obtained successively after step 301 and the presence information indicating the presence of the animal P3 at a part of the real image (step 310). On the other hand, if the animal P3 is not determined to be in the specific situation at step 309, the image generator 35 may generate a superimposing image including any of the biological information obtained successively after step 301, the presence information indicating the presence of the animal P3 at a part of the real image, and the specific information on the animal P3 recorded by the specific information recorder 32 at step 303 (step 311).

Then, the image generator 35 may transmit the superimposing image to the mobile terminal 2 or the wearable terminal 3 (step 312), and end the process of FIG. 6.

Note that if the visitor Q3 is not determined to be in front of the animal P3's exhibition place at step 308, the image generator 35 may end the process of FIG. 6 without generating any superimposing image.

Here, the superimposing image generated at step 311 of FIG. 6 and displayed on the mobile terminal 2 or the wearable terminal 3 will be described.

Figure 7:
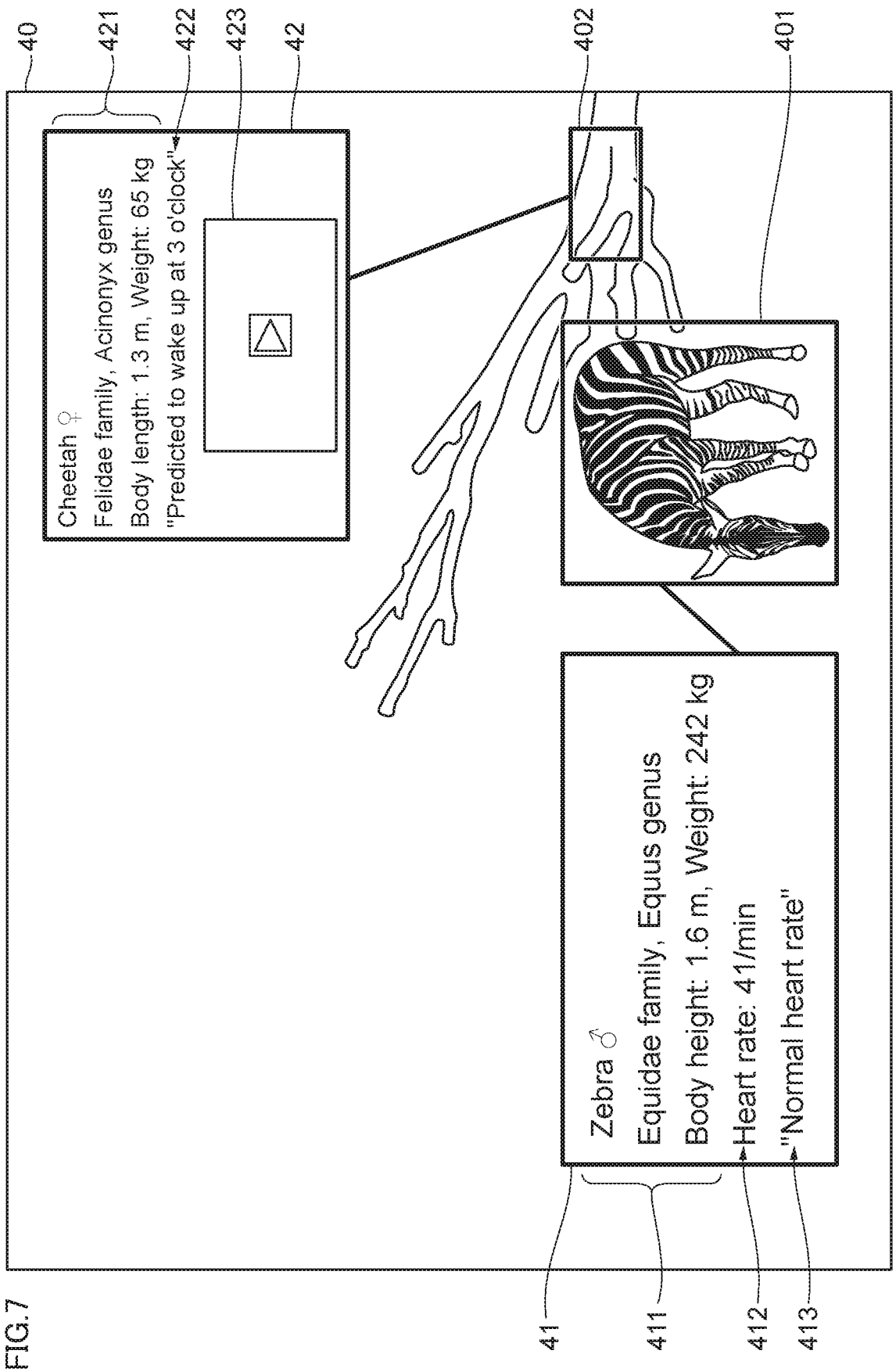
FIG. 7 depicts an example of a superimposing image displayed on a mobile terminal.

Referring to FIG. 7, there is shown an example of the superimposing image displayed on the mobile terminal 2. As shown in FIG. 7, a real image 40 may be displayed on a screen by a camera function of the mobile terminal 2, and superimposing images 41 and 42 may be superimposed on the real image 40.

The superimposing image 41 may be an image related to an animal 401. The superimposing image 41 may include a message 411 indicating a type, a sex, a body height, and a weight of the animal 401, a message 412 indicating a heart rate obtained from the biological sensor 1 for the animal 401, a message 413 indicating a state of the animal 401 judged from the heart rate.

The superimposing image 42 may be an image related to an animal 402. The animal 402 cannot be observed by being hidden behind a tree. In such a case as well, in the third embodiment, the superimposing image 42 may be displayed based on location information detected by the GPS receiver 4 attached to the animal 402, and the presence of the animal 402 may be notified to the visitor Q3. The superimposing image 42 may include a message 421 indicating a type, a sex, a body length, and a weight of the animal 402. In this example, the animal 402 is sleeping. In that case, the superimposing image 42 may include a message 422 indicating the time at which the animal 402 is predicted to wake up based on the situation prediction by the situation analyzer 31, and a video 423 recorded by the specific information recorder 32.

Figure 8:
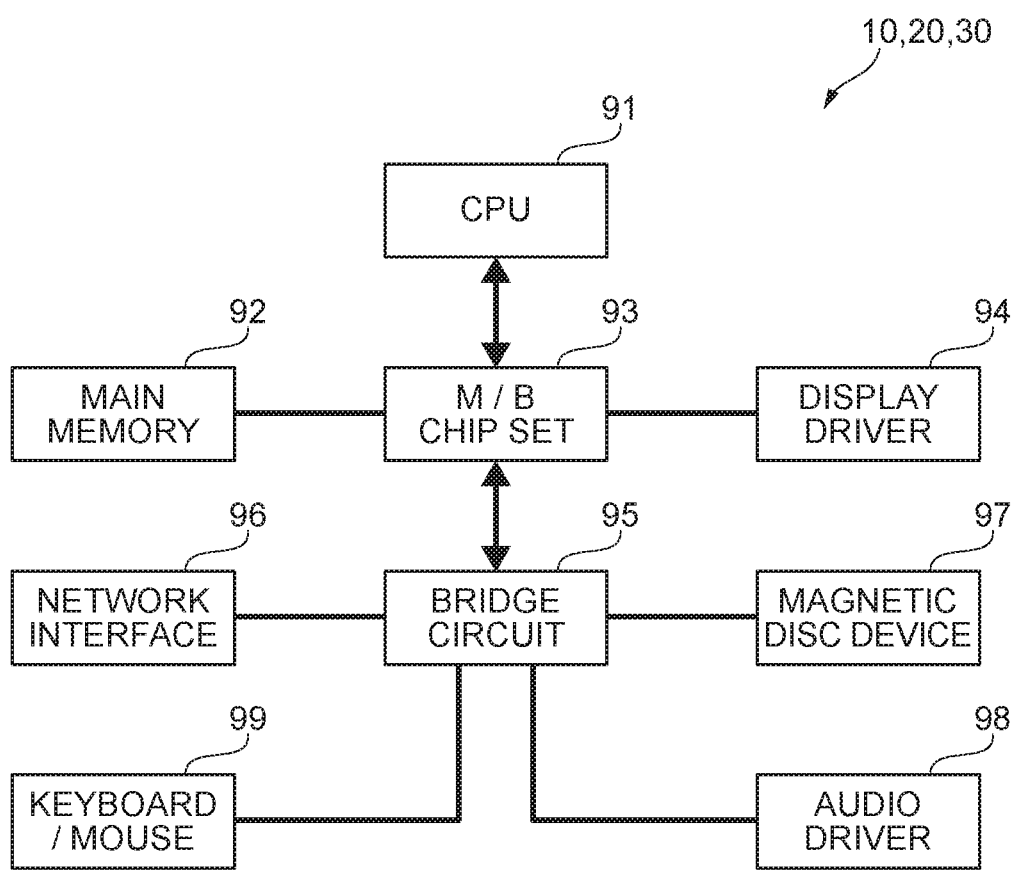
FIG. 8 depicts an example of a hardware configuration of the biological information processing device.

Referring to FIG. 8, there is shown an example of a hardware configuration 40 of each of the biological information processing devices 10 to 30 in the depicted embodiments. As shown in the figure, each of the biological information processing devices 10 to 30 may include a central processing unit (CPU) 91 serving as one example of a processor, a main memory 92 connected to the CPU 91 via a motherboard (MB) chip set 93 and serving as one example of a memory, and a display driver 94 connected to the CPU 91 via the same MB chip set 93. A network interface 96, a magnetic disk device 97, an audio driver 98, and a keyboard/mouse 99 are also connected to the MB chip set 93 via a bridge circuit 95.

In FIG. 8, the various configurational elements are connected via buses. For example, the CPU 91 and the M/B chip set 93, and the M/B chip set 93 and the main memory 92 are connected via CPU buses, respectively. Also, the MB chip set 93 and the display driver 94 may be connected via an accelerated graphics port (AGP). However, when the display driver 94 includes a PCI express-compatible video card, the MB chip set 93 and the video card are connected via a PCI express (PCIe) bus. Also, when the network interface 96 is connected to the bridge circuit 95, a PCI Express may be used for the connection, for example. For connecting the magnetic disk device 97 to the bridge circuit 95, a serial AT attachment (ATA), a parallel-transmission ATA, or peripheral components interconnect (PCI) may be used. For connecting the keyboard/mouse 99 to the bridge circuit 95, a universal serial bus (USB) may be used.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be accomplished as one step, executed concurrently, substantially concurrently, in a partially or wholly temporally overlapping manner, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A computer-implemented method for presenting information on an object to be observed, the computer-implemented method comprising:
    obtaining, by one or more processors, data from a sensor operably affixed to an object;
    predicting, by one or more processors, a time period in which the object is expected to be at a location and in a state, based on historical data obtained from the sensor;
    determining, by one or more processors, that a user is at a position to observe the location within the predicted time period;
    determining, by one or more processors, whether the object is at the location and in the state within the predicted time period; and
    responsive to determining that the user is at the position to observe the location within the predicted time period, presenting, by one or more processors, information about the object to the user, wherein the information presented varies based on the determination of whether the object is at the location and in the state within the predicted time period.

2. The computer-implemented method of claim 1, further comprising:
    recording, by one or more processors, a video of the object at a previous time period in which the object was at the location and in the state, based on data obtained from the sensor at the previous time period; and
    wherein responsive to determining that the object is not at the location and the object is not in the state, the information comprises the video of the object at the previous time period in which the object was at the location and in the state.

3. The computer-implemented method of claim 1, wherein responsive to determining that the object is at the location and the object is in the state, the information comprises text information describing the object.

4. The computer-implemented method of claim 3, wherein the information is superimposed at the location on a real image displayed on a screen of a mobile device, the real image from a camera function of the mobile device, via augmented reality.

5. The computer-implemented method of claim 1, wherein the sensor is a biological sensor and the object is living.

6. The computer-implemented method of claim 1, further comprising:
    generating, by one or more processors, an event based on the data from the sensor about the object, wherein the event adjusts a recommended route of the user.

7. The computer-implemented method of claim 1, wherein:
    responsive to determining that the object is not at the location within the predicted time period, the presented information exceeding an amount of information that would have been presented if the object was determined to be at the location at the predicted time period.

8. The computer-implemented method of claim 1, further comprising:
    actuating, by one or more processors, equipment at the location.

9. The computer-implemented method of claim 1, wherein the equipment is selected from the group consisting of: a feeding machine, a lighting device, a notification device, and a raisable bed.

10. A computer program product for presenting information on an object to be observed, the computer program product comprising:
one or more computer readable storage media and program instructions stored on the one or more computer readable storage media, the program instructions comprising:
program instructions to obtain information from a sensor operably affixed to an object;
program instructions to predict a time period in which the object is expected to be at a location and in a state, based on historical data obtained from the sensor;
program instructions to determine that a user is at a position to observe the location within the predicted time period;
program instructions to determine whether the object is at the location and in the state within the predicted time period; and
program instructions to, responsive to determining that the user is at the position to observe the location within the predicted time period, present information about the object to the user, wherein the information presented varies based on the determination of whether the object is at the location and in the state within the predicted time period.

11. The computer program product of claim 10, further comprising:
program instructions, stored on the one or more computer readable storage media, to record a video of the object at a previous time period in which the object was at the location and in the state, based on data obtained from the sensor at the previous time period; and
wherein responsive to determining that the object is not at the location and the object is not in the state, the information comprises the video of the object at the previous time period in which the object was at the location and in the state.

12. The computer program product of claim 10, wherein responsive to determining that the object is at the predetermined location and the object is in the state, the information comprises text information describing the object.

13. The computer program product of claim 12, wherein the information is superimposed at the location on a real image displayed on a screen of a mobile device, the real image from a camera function of the mobile device, via augmented reality.

14. The computer program product of claim 10, wherein the sensor is a biological sensor and the object is living.

15. The computer program product of claim 10, further comprising:
program instructions, stored on the one or more computer readable storage media, to generate an event based on the data from the sensor about the object, wherein the event adjusts a recommended route of the user.

16. A computer system for presenting information on an object to be observed, the computer system comprising:
one or more computer processors, one or more readable storage media, and program instructions stored on the one or more computer readable storage media for execution by at least one of the one or more processors, the program instructions comprising:
program instructions to obtain information from a sensor operably affixed to an object;
program instructions to predict a time period in which the object is expected to be at a location and in a state, based on historical data obtained from the sensor;
program instructions to determine that a user is at a position to observe the location within the predicted time period;
program instructions to determine whether the object is at the location and in the state within the predicted time period; and
program instructions to, responsive to determining that the user is at the position to observe the location within the predicted time period, present information about the object to the user, wherein the information presented varies based on the determination of whether the object is at the location and in the state within the predicted time period.

17. The computer system of claim 16, further comprising:
program instructions, stored on the one or more computer readable storage media for execution by at least one of the one or more processors, to record a video of the object at a previous time period in which the object was at the location and in the state, based on data obtained from the sensor at the previous time period; and
wherein responsive to determining that the object is not at the location and the object is not in the state, the information comprises the video of the object at the previous time period in which the object was at the location and in the state.

18. The computer system of claim 16, wherein responsive to determining that the object is at the predetermined location and the object is in the state, the information comprises text information describing the object.

19. The computer system of claim 16, wherein the sensor is a biological sensor and the object is living.

20. The computer program product of claim 16, further comprising:
program instructions, stored on the one or more computer readable storage media for execution by at least one of the one or more processors, to generate an event based on the data from the sensor about the object, wherein the event adjusts a recommended route of the user.

* * * * *